United States Patent [19]

Kida et al.

[11] Patent Number: 4,521,638

[45] Date of Patent: Jun. 4, 1985

[54] PROCESS FOR PREPARATION OF TERTIARY OLEFINS

[75] Inventors: Koichi Kida; Tetsuo Aoyama; Takako Uchiyama, all of Niigata, Japan

[73] Assignee: Mitsubishi Gas Chemical Company, Inc., Tokyo, Japan

[21] Appl. No.: 580,633

[22] Filed: Feb. 16, 1984

[30] Foreign Application Priority Data

Feb. 26, 1983 [JP] Japan .................................. 58-31373

[51] Int. Cl.³ ........................... C07C 1/00; C07C 1/20
[52] U.S. Cl. ..................................... 585/640; 585/639
[58] Field of Search ................................ 585/639, 640

[56] References Cited

U.S. PATENT DOCUMENTS

| 3,121,124 | 2/1964 | Verdor ................................. 585/639 |
| 4,320,232 | 3/1982 | Volkamer et al. .................. 585/639 |
| 4,343,959 | 8/1982 | Kida et al. .......................... 585/640 |

*Primary Examiner*—Delbert E. Gantz
*Assistant Examiner*—Chung K. Pak
*Attorney, Agent, or Firm*—Wenderoth, Lind & Ponack

[57] ABSTRACT

Disclosed is a process for the preparation of tertiary olefins which comprises catalytically decomposing a tertiary ether to a tertiary olefin, wherein the catalytic decomposition of the tertiary olefin is carried out in the presence of a solid phosphoric acid catalyst which has been calcined at a temperature of at least 500° C. in an inert gas.

20 Claims, No Drawings

PROCESS FOR PREPARATION OF TERTIARY OLEFINS

BACKGROUND OF THE INVENTION (1) Field of the Invention

The present invention relates to a process for preparing from a tertiary ether a corresponding tertiary olefin. More particularly, the present invention relates to a process for preparing a tertiary olefin having a high purity in a high yield from a tertiary ether by using a novel catalyst.

(2) Description of the Prior Art

Tertiary olefins have industrially been prepared from $C_4$-fractions containing tertiary olefins according to the sulfuric acid extraction process. However, this sulfuric acid extraction process is defective in that since the apparatus is corroded by the concentrated sulfuric acid used, an expensive material should be used for the apparatus and that a tertiary olefin is consumed for side reactions such as polymerization and hydration during the extraction with concentrated sulfuric acid. Therefore, this process is not advantageous from an economical viewpoint.

Recently, in U.S.A. and European countries, methyl-t-butyl ether (hereinafter referred to as "MTBE") is produced in large quantities as an octane number booster for gasoline, and there is a strong indication of the production of MTBE in Japan and there is a good possibility that MTBE will be available at a cost as low as that of gasoline. In this case, it is expected that a process for preparing isobutylene by decomposition of MTBE will become very advantageous over the sulfuric acid extraction process.

As one premise for realizing this process, it is necessary that the decomposition reaction of MTBE should be advanced at a high conversion (high decomposition ratio) with a high selectivity, and it is preferred that isobutylene and methanol obtained as decomposition products should have a high enough purity for them to be used as industrial materials.

A tertiary olefin such as isobutylene is industrially valuable as a starting material of, for example, methyl methacrylate or a butyl rubber polymer. In the latter case, it is required that the purity of isobutylene should be especially high.

Several processes have heretofore been proposed for preparing tertiary olefins from tertiary ethers. For example, Japanese Patent Publication No. 41882/72 discloses a process in which MTBE is decomposed by using a γ-alumina type acidic solid catalyst having a specific surface area of at least 25 m²/g, Japanese Patent Application Laid-Open Specification No. 39604/76 proposes a process using as a catalyst activated alumina modified by reaction with a silicon compound, Japanese Patent Application Laid-Open Specification No. 2695/80 discloses a process using a catalyst comprising silica as the main component and various metal oxides combined therewith, Japanese Patent Application Laid-Open Specification No. 94602/74 proposes a process using an active carbon catalyst, Japanese Patent Publication No. 26401/76 teaches a process using a metal sulfate as a catalyst, Japanese Patent Application Laid-Open Specification No. 85323/82 proposes a process in which an aluminum-containing silica catalyst formed, for example, by supporting aluminum sulfate on a silica carrier is used and water and/or a tertiary alcohol is added to the reaction system, Japanese Patent Application Laid-Open Specification No. 75934/82 proposes a process using a catalyst formed by supporting an aluminum compound such as aluminum sulfate on silica and heating and calcining them at a temperature higher than the decomposition temperature of the aluminum compound, Japanese Patent Application Laid-Open Specification No. 102821/82 proposes a process in which the decomposition is carried out in the presence of steam by using a catalyst comprising titanium, hafnium or zirconium supported on alumina, Japanese Patent Application Laid-Open Specification No. 123124/82 teaches a process using an acidic molecular sieve as the catalyst, Japanese Patent Application Laid-Open Specification No. 134421/82 proposes a process using a catalyst formed by supporting a metal sulfate on a carrier which has been calcined at a high temperature, and Japanese Patent Application Laid-Open Specification No. 142924/82 teaches a process using a catalyst formed by supporting an aluminum compound on a carrier containing silicon oxide and heating and calcining them at a temperature higher than the decomposition temperature of the aluminum compound.

These known processes, however, are defective in various points. For example, since an ether such as dimethyl ether is formed as a by-product by dehydration of two molecules of a methanol formed by the decomposition of MTBE, the alcohol recovery ratio is low. Furthermore, the reaction temperature is very high and the preparation of catalysts is troublesome, and expensive chemicals should be used. Moreover, the catalyst life is short and the durability is insufficient. Thus, none of the catalysts heretofore proposed are industrially satisfactory.

Since the reaction of forming a tertiary olefin by decomposition of a tertiary ether is an endothermic reaction, from the energy-saving viewpoint, it is desirable that a high decomposition ratio of the tertiary ether and a high selectivity to the tertiary olefin and alcohol should simultaneously be attained at a low temperature level.

SUMMARY OF THE INVENTION

We made research with a view to overcoming the above-mentioned defects of the conventional techniques and developing an industrially valuable catalyst being excellent in the decomposition activity at low temperature and in the selectivity, having a good reproducibility, being prepared at a low cost and having a long life and a good stability. As the result, we have now completed the present invention.

More specifically, in accordance with the present invention, there is provided a process for the preparation of tertiary olefins which comprises catalytically decomposing a tertiary ether to a tertiary olefin, wherein the catalytic decomposition of the tertiary ether is carried out in the presence of a solid phosphoric acid catalyst which has been calcined at a temperature of at least 500° C. in an inert gas.

DETAILED DESCRIPTION OF THE PREFERRED EMBODIMENTS

Any of tertiary ethers mentioned above can be used in the present invention without any particular limitation. However, tertiary ethers represented by the following general formula are ordinarily used:

$$R_2-\underset{\underset{R_3}{|}}{\overset{\overset{R_1}{|}}{C}}-O-R_4$$

wherein $R_1$, $R_2$ and $R_3$, which may be the same or different, stand for an alkyl group having 1 to 4 carbon atoms, preferably an alkyl group having 1 to 3 carbon atoms, such as a methyl, ethyl or isopropyl group, and $R_4$ stands for an alkyl group having 1 to 3 carbon atoms, preferably a methyl, ethyl or isopropyl group.

Typical examples of the tertiary ether represented by the above general formula and tertiary olefins prepared therefrom are described below.

| Tertiary Ethers | Tertiary Olefins |
|---|---|
| $H_3C-\underset{\underset{CH_3}{\|}}{\overset{\overset{CH_3}{\|}}{C}}-O-CH_3 \longrightarrow$ <br> MTBE | $\underset{CH_3}{\overset{CH_3}{\diagdown}}C=CH_2$ <br> isobutylene |
| $H_3C-\underset{\underset{CH_3}{\|}}{\overset{\overset{CH_3}{\|}}{C}}-O-C_2H_5 \longrightarrow$ <br> ethyl-t-butyl ether | $\underset{CH_3}{\overset{CH_3}{\diagdown}}C=CH_2$ <br> isobutylene |
| $CH_3-CH_2-\underset{\underset{CH_3}{\|}}{\overset{\overset{CH_3}{\|}}{C}}-O-CH_3 \longrightarrow$ <br> methyl-t-amyl ether | $CH_3-\overset{\overset{CH_3}{\|}}{C}=CH-CH_3$ <br> 2-methyl-2-butene <br> (cis- and trans-forms) <br><br> $CH_2=\overset{\overset{CH_3}{\|}}{C}-CH_2-CH_3$ <br> 2-methyl-1-butene |
| $CH_3-\overset{\overset{CH_3}{\|}}{\underset{\underset{CH_3}{\|}}{C}}-H \atop CH_3-\underset{\underset{CH_3}{\|}}{C}-O-CH_3 \longrightarrow$ <br> 2,3-dimethyl-2-methoxybutane | $CH_2=\overset{\overset{CH_3}{\|}}{C}-\overset{\overset{CH_3}{\|}}{C}H-CH_3$ <br> 2,3-dimethyl-1-butene <br><br> $CH_3-\overset{\overset{CH_3}{\|}}{C}=\overset{\overset{CH_3}{\|}}{C}-CH_3$ <br> 2,3-dimethyl-2-butene |
| $CH_3-\underset{\underset{\underset{CH_3}{\|}}{\underset{CH_2}{\|}}}{\overset{\overset{CH_3}{\|}}{C}}-O-CH_3 \longrightarrow$ <br> 2-methoxy-2-methylpentane | $CH_2=\overset{\overset{CH_3}{\|}}{C}-CH_2-CH_2-CH_3$ <br> 2-methyl-1-pentene <br><br> $CH_3-\overset{\overset{CH_3}{\|}}{C}=CH-CH_2-CH_3$ <br> 2-methyl-2-pentene |
| $H_3C-\underset{\underset{\underset{CH_3}{\|}}{\underset{CH_2}{\|}}}{\overset{\overset{CH_3}{\|}}{\underset{\underset{}{\|}}{C}}}-O-CH_3 \longrightarrow$ <br> 3-methoxy-3-methylpentane | $CH_2=\overset{\overset{CH_3}{\|}}{C}-CH_2-CH_3$ <br> 2-ethyl-1-butene <br><br> $CH_3-CH=\overset{\overset{CH_3}{\|}}{C}-CH_2-CH_3$ <br> 3-methyl-2-pentene <br> (cis- and trans-forms) |

Of the foregoing tertiary ethers, MTBE, methyl-t-amyl ether and ethyl-t-butyl ether are preferred as industrial starting materials.

The process for the preparation of these ethers is not particularly critical. For example, in case of MTBE, it is possible to use MTBE prepared from isobutylene having a high purity and methanol having a high purity. However, use of MTBE prepared from a $C_4$-fraction containing isobutylene and methanol is preferred and industrially significant. More specifically, the process in which MTBE is isolated from the reaction product between the $C_4$-fraction containing isobutylene and methanol by such purification means as distillation and this MTBE is decomposed into isobutylene and methanol can be regarded as the process for subjecting the $C_4$-fraction to extraction with methanol to recover isobutylene. In short, this process can be an excellent process for purifying isobutylene.

The solid phosphoric acid catalyst used in the present invention is a catalyst formed by supporting a phosphoric acid component such as orthophosphoric acid, pyrophosphoric acid, metaphosphoric acid or polyphosphoric acid (triphosphoric acid or tetraphosphoric acid) on a carrier containing a metal oxide. As typical examples of the carrier, there can be mentioned diatomaceous earth, aluminum oxide, zirconium oxide, titanium oxide, thorium oxide, acid clay, activated clay, silica-alumina and zeolite. The carriers may be used singly or in the form of a mixture of two or more of them. These carriers are ordinarily used in the untreated state, but products formed by calcining these carriers according to customary procedures can also be used. A process comprising supporting phosphoric anhydride ($P_2O_5$), orthophosphoric acid ($H_3PO_4$) or ammonium phosphate [$(NH_4)_3PO_4$] per se or in the form of an aqueous solution on a carrier such as mentioned above and calcining is preferably adopted for the production of the catalyst. By calcination, the beforementioned phosphorus compound is partially or entirely converted to pyrophosphoric acid, metaphosphoric acid or polyphosphoric acid.

The solid phosphoric acid catalyst used in the present invention may further comprise a metal such as nickel, copper, cobalt, iron, zinc, chromium, manganese, titanium or vanadium or an oxide thereof in order to improve catalyst physical properties such as heat-conductivity, strength, attrition resistance and bulk density.

In the present invention, the lower limit of the calcination temperature is 500° C., preferably 600° C., especially preferably 700° C., but the upper limit is not particularly critical. However, the upper limit of the calcination temperature is 1200° C., preferably 1150° C., especially preferably 1100° C. If the calcination temperature is lower than 500° C., a catalyst having a sufficient activity and a long life cannot be obtained. Furthermore, after deposition of phosphoric acid on the carrier but before calcination conducted at a temperature not lower than 500° C., drying and/or low temperature calcination may be carried out at room temperature or an elevated temperature lower than 500° C. to remove a part or all of the solvent such as water, contained in the phosphoric acid-supported carrier, and this drying and/or low temperature calcination is preferred.

The calcination time is changed according to the amount supported of phosphoric acid, the calcination temperature and the kind of the carrier and is not generally defined. However, a calcination time of 0.5 to 50 hours is ordinarily sufficient. Generally, as the calcination temperature is high, the calcination time may be shortened.

The calcination is carried out in an atmosphere of an inert gas such as air, nitrogen, helium, argon, steam or a mixture thereof. From the practical viewpoint, it is most preferred that the calcination be carried out in air.

As means for depositing phosphoric acid on the carrier, there can be adopted a method comprising spraying commercially available 85% phosphoric acid or a solution formed by dissolving this phosphoric acid in a solvent such as water on the carrier, a method comprising dipping the carrier in a solution of phosphoric acid and drying the carrier, a method comprising dipping the carrier in commercially available phosphoric acid or a solution thereof and subjecting to suction filtration or centrifugal separation, and other customary methods.

The amount of phosphoric acid supported on the carrier (expressed as the amount of $P_2O_5$; the same will apply hereinafter) is changed according to the kind of the carrier and is not generally defined. From the practical viewpoint, however, the amount of phosphoric acid supported on the carrier is ordinarily adjusted to 0.5 to 200 parts by weight, preferably 1 to 100 parts by weight, per 100 parts by weight of the carrier.

The reaction of the present invention may be carried out batchwise or in a continuous manner. Ordinarily, the gas phase reaction of the fixed bed system is preferably adopted. Other systems such as the fluidized bed system may also be adopted.

The reaction is carried out at a temperature of 100° to 400° C., preferably 130° to 350° C.

The reaction pressure is not particularly critical, but ordinarily, the reaction is carried out under a pressure of from atmospheric pressure to 30 Kg/cm$^2$, preferably from atmospheric pressure to 10 Kg/cm$^2$.

The reaction time is changed according to the reaction temperature and the kind of the catalyst and is not generally defined. For example, in the continuous process, the weight hourly space velocity of the tertiary ether per unit volume of the catalyst (WHSV, g/ml of catalyst/hr; the same will apply hereinafter) is 0.3 to 100 g/ml/hr, preferably 0.5 to 30 g/ml/hr.

Steam may be present in the reaction system, and the presence of steam in the reaction system is preferred. The molar ratio of steam to the tertiary ether ($H_2O$/tertiary ether molar ratio), what is called, the steam ratio, is in the range of from 0.05 to 30, preferably from 0.1 to 20.

The catalyst of the present invention has a very long life. When the activity of the catalyst is reduced, the catalyst can easily be regenerated by heating the catalyst at a temperature higher than the reaction temperature in the presence of an inert gas such as helium, nitrogen, steam or air, and the life of the catalyst can be prolonged. It is preferred that the regeneration temperature be higher by at least 50° C. than the reaction temperature but be lower than 1100° C. It is ordinarily preferred that the high temperature inert gas be passed through the catalyst bed for the regeneration. The high temperature inert gas to be used for the regeneration may be obtained by heating the inert gas outside the catalyst bed in advance or by heating the inert gas inside the catalyst bed together with the catalyst.

The catalyst used in the present invention is prepared very simply at a low cost, and the life of the catalyst is long and the catalyst can be regenerated very easily. Furthermore, the conversion of the tertiary ether is high and the selectivities to the tertiary olefin and the alcohol are high, and the tertiary olefin having a high purity can be obtained at a high efficienty even at a low reaction temperature. Accordingly, the present invention is of great industrial importance.

The present invention will now be described in detail with reference to the following Examples that by no means limit the scope of the invention.

EXAMPLES 1 THROUGH 6

60 g of diatomaceous earth, 10 g of titanium dioxide, 35 g of commercially available 85% orthophosphoric acid and 100 g of water were sufficiently mixed, and the mixture was dried below 100° C., calcined at 200° C. for 1 hour, pulverized to a size of 14 to 32 mesh, calcined at a high temperature shown in Table 1 and then charged in a stainless steel reaction vessel.

MTBE was decomposed under a reaction pressure of 5 Kg/cm$^2$ in the presence or absence of steam.

The obtained results are shown in Table 1.

TABLE 1

|  | Example No. | | | | | |
| --- | --- | --- | --- | --- | --- | --- |
|  | 1 | 2 | 3 | 4 | 5 | 6 |
| Calcination temperature (°C.) | 900 | 1000 | 800 | 900 | 900 | 1100 |
| Calcination time (hours) | 18 | 10 | 24 | 18 | 18 | 2 |
| Steam ratio ($H_2O$/MTBE molar ratio) | 5 | 5 | 5 | 2 | no steam | 5 |
| Reaction temperature (°C.) | 190 | 190 | 190 | 190 | 240 | 190 |
| WHSV (g/ml/hr) | 4 | 4 | 4 | 4 | 4 | 4 |
| Conversion (%) MTBE | 99.7 | 99.6 | 99.8 | 99.9 | 98.9 | 99.2 |
| Selectivities (&) | | | | | | |
| isobutylene | 99.5 | 99.6 | 99.5 | 99.6 | 99.1 | 99.7 |
| di-isobutylene | 0.05 | 0.01 | 0.1 | 0.15 | 0.8 | 0.01 |
| t-butanol | 0.45 | 0.39 | 0.4 | 0.25 | 0.1 | 0.29 |
| methanol | 100 | 100 | 100 | 100 | 99.8 | 100 |
| dimethyl ether | 0 | 0 | 0 | 0 | 0.2 | 0 |

From the foregoing experimental results, it will readily be understood that the effects of the present invention can be increased when a solid phosphoric acid catalyst calcined at a high temperature is used, and that the effects can further be enhanced when steam is present in the reaction system.

EXAMPLE 7

A commercially available silica carrier (N-608 supplied by Nikki Kagaku) was pulverized to a size of 14 to 32 mesh. Then, 70 g of this silica carrier was dipped in an aqueous solution containing 35 g of commercially available 85% orthophosphoric acid, and water was evaporated at a temperature lower than 100° C. and calcination was conducted at 200° C. for 1 hour and at 900° C. for 18 hours. A stainless steel reaction vessel was charged with 13 ml of the so-obtained catalyst.

MTBE was supplied at WHSV of 4 g/ml/hr under conditions of a steam ratio of 5.0, a reaction pressure of 5.0 Kg/cm$^2$ and a reaction temperature of 201° C. The conversion of MTBE was 99.6%, the selectivity to isobutylene was 99.2%, the selectivity to di-isobutylene was 0.2%, the selectivity to t-butanol was 0.6%, and the selectivity of methanol was 100%. Formation of dimethyl ether was not observed at all.

EXAMPLES 8 THROUGH 14

Commercially available silica-alumina (N-631L supplied by Nikki Kagaku) was pulverized to a size of 14 to 32 mesh. Then, 85 g of this silica-alumina was dipped in an aqueous solution containing 18 g of commercially available 85% orthophosphoric acid, dried below 100° C., calcined at 200° C. for 1 hour and then calcined at a high temperature of 1000° C. for 6 hours. A stainless steel reaction tube was charged with 13 ml of the so-prepared catalyst.

MTBE was decomposed in the presence of steam by changing the steam ratio, reaction temperature, reaction pressure and WHSV.

The obtained results are shown in Table 2.

TABLE 2

| | Example No. | | | | | | |
|---|---|---|---|---|---|---|---|
| | 8 | 9 | 10 | 11 | 12 | 13 | 14 |
| Reaction pressure (Kg/cm$^2$) | 5 | 5 | 5 | atmospheric pressure | 5 | 5 | |
| Reaction temperature (°C.) | 200 | 200 | 200 | 200 | 220 | 210 | 190 |
| Steam ratio | 7 | 5 | 3 | 5 | 5 | 7 | 7 |
| WHSV (g/ml/hr) | 4 | 4 | 4 | 4 | 6 | 5 | 4 |
| Conversion (%) of MTBE | 99.7 | 99.8 | 99.8 | 99.8 | 99.7 | 99.8 | 99.5 |
| Selectivities (%) | | | | | | | |
| isobutylene | 99.4 | 99.5 | 99.5 | 99.6 | 99.5 | 99.5 | 99.4 |
| di-isobutylene | 0.1 | 0.1 | 0.2 | 0.1 | 0.2 | 0.1 | 0.1 |
| t-butanol | 0.4 | 0.4 | 0.3 | 0.3 | 0.3 | 0.4 | 0.5 |
| methanol | 100 | 100 | 100 | 100 | 100 | 100 | 100 |
| dimethyl ether | 0 | 0 | 0 | 0 | 0 | 0 | 0 |

EXAMPLE 15

The catalyst life test was carried out under the same reaction conditions as adopted in Example 13 by using the same catalyst as used in Example 13.

The obtained results are shown in Table 3.

TABLE 3

| Reaction Time (hours) | Conversion (%) of MTBE | Selectivity (%) to Iso-butylene | Selectivity (%) to Methanol |
|---|---|---|---|
| 6 | 99.8 | 99.5 | 100 |
| 142 | 99.8 | 99.5 | 100 |
| 480 | 99.6 | 99.5 | 100 |

TABLE 3-continued

| Reaction Time (hours) | Conversion (%) of MTBE | Selectivity (%) to Iso-butylene | Selectivity (%) to Methanol |
|---|---|---|---|
| 801 | 99.5 | 99.6 | 100 |
| 1007 | 99.3 | 99.6 | 100 |
| 2100 | 98.8 | 99.7 | 100 |
| 4005 | 98.3 | 99.7 | 100 |

From the results shown in Table 3, it will readily be understood that the catalyst of the present invention exerts excellent conversion and selectivity over a long period.

EXAMPLE 16

The reaction was carried out in the same manner as in Example 8 except that ethyl-t-butyl ether was used instead of MTBE. The conversion of ethyl-t-butyl ether was 99.5%, the selectivity to isobutylene was 99.5%, the selectivity to di-isobutylene was 0.1%, the selectivity to t-butanol was 0.4%, and the selectivity to ethanol was 100%. Formation of diethyl ether was not observed at all.

COMPARATIVE EXAMPLE 1

The same catalyst as prepared in Examples 1 through 6 was calcined at 400° C. for 18 hours and charged in a stainless steel reaction tube, and the reaction was carried out under conditions of a steam ratio of 5, a reaction temperature of 190° C., WHSV 4.0 g/ml/hr and a reaction pressure of 5.0 Kg/cm$^2$. The conversion of MTBE was 98.0%, the selectivity to isobutylene was 98.5%, the selectivity to di-isobutylene was 1.0%, the selectivity to t-butanol was 0.5%, the selectivity to methanol was 99.5%, and the selectivity to dimethyl ether was 0.5%.

COMPARATIVE EXAMPLE 2

By using the same catalyst as prepared in Example 15, the catalyst life test was carried out in the same manner as described in Example 15 except that the calcination temperature was changed to 400° C. and the calcination time was changed to 24 hours.

The obtained results are shown in Table 4.

TABLE 4

| Reaction Time (hours) | Conversion (%) of MTBE | Selectivity (%) to Iso-butylene | Selectivity (%) to Methanol |
|---|---|---|---|
| 6 | 99.0 | 98.7 | 99.5 |
| 140 | 98.7 | 98.8 | 99.6 |
| 500 | 95.0 | 99.3 | 99.9 |

COMPARATIVE EXAMPLE 3

Commercially available silica-alumina (N-631L supplied by Nikki Kagaku) was pulverized to 14 to 32 mesh. This silica-alumina was calcined at 1000° C. for 6 hours. A stainless steel reaction tube was charged with 13 ml of this silica-alumina.

The reaction was carried out at a steam ratio of 5, a reaction pressure of 5 Kg/cm$^2$ and a reaction temperature of 200° C. while maintaining WHSV of MTBE at 1.5 g/ml/hr. The conversion of MTBE was 91.0%.

From this result, it is seen that the solid phosphoric acid catalyst of the present invention has a very high effect.

COMPARATIVE EXAMPLE 4

Commercially available silica-alumina (N-631L supplied by Nikki Kagaku) was calcined at 1000° C. for 6 hours, and by using this silica-alumina as the catalyst, the reaction was carried out under the same conditions as described in Example 15.

The obtained results are shown in Table 5.

TABLE 5

| Reaction Time (hours) | Conversion (%) of MTBE | Selectivity (%) to Isobutylene | Selectivity (%) to Methanol |
|---|---|---|---|
| 10 | 94.5 | 99.4 | 100 |
| 138 | 94.3 | 99.4 | 100 |
| 480 | 94.0 | 99.5 | 100 |
| 750 | 93.2 | 99.6 | 100 |
| 1001 | 90.6 | 99.6 | 100 |

We claim:

1. In a process for the preparation of tertiary olefins which comprises catalytically decomposing a tertiary ether to a tertiary olefin, the improvement wherein the catalytic decomposition of the tertiary olefin is carried out in the presence of a solid phosphoric acid catalyst which has been calcined at a temperature not lower than 500° C. in an inert gas, said decomposition being carried out in the presence of steam.

2. A process for the preparation of tertiary olefins according to claim 1, wherein the tertiary ether is a compound represented by the following general formula:

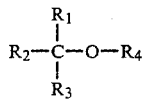

wherein $R_1$, $R_2$ and $R_3$, which may be the same or different, stand for an alkyl group having 1 to 4 carbon atoms, and $R_4$ stands for an alkyl group having 1 to 3 carbon atoms.

3. A process for the preparation of tertiary olefins according to claim 1, wherein the tertiary ether is methyl-t-butyl ether, methyl-t-amyl ether or ethyl-t-butyl ether.

4. A process for the preparation of tertiary olefins according to claim 1, wherein the phosphoric acid component of the solid phosphoric acid catalyst is orthophosphoric acid, pyrophosphoric acid, metaphosphoric acid or polyphosphoric acid.

5. A process for the preparation of tertiary olefins according to claim 1, wherein the solid phosphoric acid catalyst is derived from orthophosphoric acid.

6. A process for the preparation of tertiary olefins according to claim 1, wherein the carrier of the solid phosphoric acid catalyst is a carrier containing a metal oxide.

7. A process for the preparation of tertiary olefins according to claim 1, wherein the carrier of the solid phosphoric acid catalyst is diatomaceous earth, aluminum oxide, zirconium oxide, titanium oxide, thorium oxide, acid clay, activated clay, silica-aluminia or zeolite.

8. A process for the preparation of tertiary olefins according to claim 1, wherein the solid phosphoric acid catalyst contains nickel, copper, cobalt, iron, zinc, chromium, manganese or vanadium.

9. A process for the preparation of tertiary olefins according to claim 1, wherein the calcination of the solid phosphoric acid catalyst is carried out at a temperature of 500° to 1200° C.

10. A process for the preparation of tertiary olefins according to claim 1, wherein the solid phosphoric acid catalyst is one that has been dried and calcined at a low temperature of from room temperature to a temperature of lower than 500° C. and then calcined at a temperature of at least 500° C.

11. A process for the preparation of tertiary olefins according to claim 1, wherein the calcination of the solid phosphoric acid catalyst is conducted for 0.5 to 50 hours.

12. A process for the preparation of tertiary olefins according to claim 1, wherein the inert gas is air, nitrogen, helium, argon or steam.

13. A process for the preparation of tertiary olefins according to claim 1, wherein the solid phosphoric acid catalyst is one formed by supporting phosphoric acid on a support in an amount of 0.5 to 200 parts by weight as $P_2O_5$ per 100 parts by weight of the carrier.

14. A process for the preparation of tertiary olefins according to claim 1, wherein the decomposition reaction temperature is in the range of from 100 to 400° C.

15. A process for the preparation of tertiary olefins according to claim 1, wherein the decomposition reaction pressure is in the range of from atmospheric pressure to 30 Kg/cm$^2$.

16. A process for the preparation of tertiary olefins according to claim 1, wherein the weight hourly space velocity (WHSV) of the tertiary ether per unit volume of the catalyst is 0.3 to 100 g/ml of catalyst/hr.

17. A process for the preparation of tertiary olefins according to claim 1, wherein the molar ratio of steam ($H_2O$) to the tertiary ether is in the range of from 0.05 to 30.

18. In a process for the preparation of tertiary olefins which comprises catalytically decomposing a tertiary ether to a tertiary olefin, the improvement wherein the catalytic decomposition of the tertiary ether to the tertiary olefin is carried out in the presence of a solid phosphoric acid catalyst which has been calcined at a temperature not lower than 500° C. in an inert gas, said decomposition being carried out in the presence of steam, and when the activity of the catalyst is lowered, the catalyst is regenerated by heating it at a temperature higher than the reaction temperature in the presence of an inert gas.

19. A process for the preparation of tertiary olefins according to claim 18, wherein the inert gas used for the regeneration is helium, nitrogen, steam or air.

20. A process for the preparation of tertiary olefins according to claim 18, wherein the regeneration temperature is higher by at least 50° C. than the decomposition reaction temperature but lower than 1100° C.

* * * * *

UNITED STATES PATENT AND TRADEMARK OFFICE
CERTIFICATE OF CORRECTION

PATENT NO. : 4,521,638
DATED : June 4, 1985
INVENTOR(S) : Koichi KIDA, Tetsuo AOYAMA and Takako UCHIYAMA It is certified that error appears in the above—identified patent and that said Letters Patent is hereby corrected as shown below:

In the Abstract, line 4, change "olefin" to -- ether -- .

IN THE CLAIMS

Claim 1, line 4, change "olefin" to -- ether -- .

Signed and Sealed this

Eleventh Day of February 1986

[SEAL]

Attest:

DONALD J. QUIGG

Attesting Officer

Commissioner of Patents and Trademarks